United States Patent
Hermine et al.

(10) Patent No.: US 9,675,590 B2
(45) Date of Patent: Jun. 13, 2017

(54) METHODS AND PHARMACEUTICAL COMPOSITIONS FOR THE TREATMENT OF MYELODYSPLASTIC SYNDROMES

(71) Applicants: INSERM (INSTITUT NATIONAL DE LA SANTÉ ET DE LA RECHERCHE MÉDICALE), Paris (FR); FONDATION IMAGINE, Paris (FR); ASSISTANCE PUBLIQUE-HÔPITAUX DE PARIS (APHP), Paris (FR); UNIVERSITÉ PARIS DESCARTES, Paris (FR); CENTRE NATIONAL DE LA RECHERCHE SCIENTIFIQUE (CNRS), Paris (FR)

(72) Inventors: Olivier Hermine, Paris (FR); Flavia Guillem, Paris (FR); Jean-Benoit Arlet, Paris (FR); Geneviève Courtois, Paris (FR); Michaela Fontenay, Paris (FR)

(73) Assignees: Institut National de la Sante et de la Recherche Medicale (INSERM), Paris (FR); Fondation Imagine, Paris (FR); Assistance Publique-Hopitaux de Paris (APHP), Paris (FR); Universite Paris Descartes, Paris (FR); Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 15/316,890

(22) PCT Filed: Jun. 9, 2015

(86) PCT No.: PCT/EP2015/062807
§ 371 (c)(1),
(2) Date: Dec. 7, 2016

(87) PCT Pub. No.: WO2015/189186
PCT Pub. Date: Dec. 17, 2015

(65) Prior Publication Data
US 2017/0100378 A1    Apr. 13, 2017

(30) Foreign Application Priority Data
Jun. 10, 2014 (EP) .................... 14305873

(51) Int. Cl.
*A61K 31/422* (2006.01)
*A61K 31/366* (2006.01)

(52) U.S. Cl.
CPC .......... *A61K 31/422* (2013.01); *A61K 31/366* (2013.01)

(58) Field of Classification Search
None
See application file for complete search history.

(56) References Cited

PUBLICATIONS

Savona et al., "Phase I Trial of Selinexor (KPT033), A First-In-Class Oral Selective Inhibitor of Nuclear Export (SINE) In Patients (pts) With Advanced Myelogenous Leukemia (Aml)", Database Biosis, Nov. 15, 2013, Philadelphia, PA.
Savona et al., "Phase I Trial of Selinexor (KPT033), A First-In-Class Oral Selective Inhibitor of Nuclear Export (SINE) In Patients (pts) With Advanced Myelogenous Leukemia (AML)", 55th ASH Annual Meeting and Exposition, Dec. 7, 2013, Web.
Ribeil et al., "Hsp70 regulates erythropoiesis by preventing caspase-3-mediated cleavage of GATA-1", Nature, Dec. 10, 2016, pp. 102-105, vol. 445, No. 7123.
Tai et al., "CRM1 inhibition induces tumor cell cytotoxicity and impairs osteoclastogenesis in multiple myeloma: molecular mechanisms and therapeutic implications", Leukemia, Apr. 16, 2013, pp. 155-165, vol. 28, No. 1.
Schmidt et al., "Genome-wide studies in multiple myeloma identify XP01/CRM1 as a critical target validated using the selective nuclear export inhibitor KPT-276", Leukemia, Jun. 11, 2013, pp. 2357-2365, vol. 27, No. 12.
Zhong et al., "Selinexor suppresses downstream effectoors of B-cell activation, proliferation and migration in chronic lymphocytic leukemia cells", Leukemia, Jan. 13, 2014, vol. 28, No. 5.

*Primary Examiner* — Brian J Davis
(74) *Attorney, Agent, or Firm* — Whitham Curtis & Cook, PC (57) ABSTRACT

The present invention provides methods and pharmaceutical compositions designed to intervene in this defective process and to promote or restore erythrocyte maturation in individuals suffering from a myelodysplastic syndrome. The methods involve maintaining the activity of GATA-1 by preventing sequestration of Hsp70 in the cytoplasm. Accordingly, it is an object of this invention to provide methods of restoring or increasing erythrocyte maturation in a subject suffering from a myelodysplastic syndrome by preventing proteolytic inactivation of GATA-1. In some embodiments, preventing is achieved by administering to the subject a compound that inhibits the XPO1 nuclear transporter.

2 Claims, 4 Drawing Sheets

METHODS AND PHARMACEUTICAL COMPOSITIONS FOR THE TREATMENT OF MYELODYSPLASTIC SYNDROMES

FIELD OF THE INVENTION

The present invention relates to methods and pharmaceutical compositions for the treatment of myelodysplastic syndromes.

BACKGROUND OF THE INVENTION

Myelodysplastic syndromes (MDS) are clonal disorders of the HSC characterized by ineffective hematopoiesis leading to peripheral blood cytopenias, mainly anemia. Erythroid cell dysplasia is observed in 50% of early stage MDS, including refractory anemia (RA), refractory cytopenia with (RCMD) or without multilineage dysplasia, 5q-syndrome, refractory anemia with ring sideroblasts (RARS or RCMD-RS), and RA with excess of blasts (RAEB) with <10% medullary blasts (RAEB 1). Dyserythropoiesis associates with a defective maturation of erythroid precursors and an excessive apoptosis. The initial erythropoietic cell damage differs among MDS subtypes, for example, 5q-syndrome involves RPS14 haploinsufficiency, defective ribosomal biogenesis, and p53 activation, while RARS includes aberrant iron accumulation and mitochondrial stress.

Commitment of the BM progenitor cells is achieved through expression of lineage-specific transcription factors. GATA-1 is a zinc finger hematopoietic transcription factor expressed in erythroid cells, megakaryocytes, mast cells, and eosinophils. This transcription factor is required for the commitment of multipotent hematopoietic progenitor to the erythroid and megakaryocytic lineages. Mutant embryonic stem cells deleted of GATA-1 fail to give rise to mature RBCs in vitro. Deletion of GATA-1 gene in mice results in a lethal phenotype between embryonic day (E) 10.5 and E11.5 because of severe anemia. GATA-1 mutated embryos at E9.5 contain erythroid cells arrested at an early proerythroblast-like stage of their differentiation, thus demonstrating that GATA-1 is also required for the terminal erythroid cell maturation. Recently, it has been shown that alteration of Hsp70 cytosolic-nuclear shuttling is a major feature of MDS that favors GATA-1 cleavage and differentiation impairment, but not apoptosis, in dysplastic erythroblasts. Accordingly compounds which are able to restore nuclear localization of Hsp70 are highly desirable for resorting erythrocyte maturation in individuals suffering from MDS.

SUMMARY OF THE INVENTION

The present invention provides methods and pharmaceutical compositions designed to intervene in this defective process and to promote or restore erythrocyte maturation in individuals suffering from a myelodysplastic syndrome. The methods involve maintaining the activity of GATA-1 by preventing sequestration of Hsp70 in the cytoplasm. Accordingly, it is an object of this invention to provide methods of restoring or increasing erythrocyte maturation in a subject suffering from a myelodysplastic syndrome by preventing proteolytic inactivation of GATA-1. In some embodiments, preventing is achieved by administering to the subject a compound that inhibits the XPO1 nuclear transporter.

DETAILED DESCRIPTION OF THE INVENTION

The present invention relates to an XPO1 inhibitor for use in a method for treating a myelodysplastic syndrome in a subject in need thereof. The present invention relates to an XPO1 inhibitor for use in a method for promoting or restoring erythrocyte maturation in a subject suffering from a myelodysplastic syndrome.

As used herein, the term "myelodysplastic syndrome" or "MDS" has its general meaning in the art. MDS are a group of disorders characterized by one or more peripheral blood cytopenias secondary to bone marrow dysfunction. The syndromes may arise de novo, or following treatment with chemotherapy and/or radiation therapy. Secondary myelodysplasia usually has a poorer prognosis than does de novo myelodysplasia. Prognosis may be related to the number of bone marrow blast cells and to the degree of peripheral blood cytopenias. The MDS transforms to acute myeloid leukemia (AML) in about 30% of patients after various intervals from diagnosis, and at variable rates. Classification systems of MDS include the French-American-British (FAB) classification system, and the World Health Organization (WHO) classification system, which rely on the appearance of particular cells in the bone marrow.

As used herein the term "XPO1" has its general meaning in the art and refers to the exportin 1 protein. The protein mediates leucine-rich nuclear export signal (NES)-dependent protein transport. The protein is also called Chromosomal Region Maintenance 1 (Crm1).

As used herein the term "XPO1 inhibitor" has its general meaning in the art and designates any compound or treatment that reduces or blocks the activity of XPO1. The term also includes inhibitors of XPO1 expression.

XPO1 inhibitors are well known in the art as illustrated by Etchin et al., 2013; Schmidt et al., 2013; Turner et al., 2014; Fung and Chook, 2014; Senapedis et al., 2014; Mao and Yang, 2013; Gravina et al., 2014.

In certain embodiments of the invention the XPO1 inhibitor is selected from small molecule compounds that have been disclosed in the following publications WO2011109799, WO2012099807, WO2013020024, WO 2013019548, and WO2013019561.

In some embodiments, the XPO1 inhibitor is selected from the group consisting of the following compounds:

and pharmaceutically acceptable salts thereof.

In some embodiments, the XPO1 inhibitor is selected from the group consisting of (Z)-3-[3-(3-Chloro-phenyl)-[1,2,4]-triazol-1-yl]-acrylic acid ethyl ester; (E)-3-[3-(3-Chloro-phenyl)-[1,2,4]-triazol-1-yl]-acrylic acid ethyl ester; (Z)-3-[3-(3-Chloro-phenyl)-[1,2,4]-triazol-1-yl]-acrylic acid isopropyl ester; (E)-3-[3-(3-Chloro-phenyl)-[1,2,4]-triazol-1-yl]-acrylic acid isopropyl ester; (Z)-3-[3-(3-Chloro-phenyl)-[1,2,4]-triazol-1-yl]-acrylic acid tert-butyl ester; (Z)-3-[3-(3-Chloro-phenyl)-[1,2,4]-triazol-1-yl]-acrylic acid tert-butyl ester; (E)-3-[3-(3-Chloro-phenyl)-[1,2,4]-triazol-1-yl]-N-phenyl-acryl amide; (E)-N-(2-Chloro-phenyl)-3-[3-(3-chloro-phenyl)-[1,2,4]-triazol-1-yl]-acryl amide; (4-{(E)-3-[3-(3-Chloro-phenyl)-[1,2,4]-triazol-1-yl]-acryloylamino}-phenyl)-carbamic acid tert-butyl ester; (E)-3-[3-(3-Chloro-phenyl)-[1,2,4]-triazol-1-yl]-N-(4-methoxy-phenyl)-acryl amide; (E)-3-[3-(3-Chloro-phenyl)-[1,2,4]-triazol-1-yl]-N-methyl-N-phenyl-acryl amide; (E)-3-[3-(3-Chloro-phenyl)-[1,2,4]-triazol-1-yl]-N-methyl-N-phenyl-acryl amide; (E)-N-(4-Amino-phenyl)-3-[3-(3-chloro-phenyl)-[1,2,4]-triazol-1-yl]-acryl amide and pharmaceutically-acceptable salts thereof.

In some embodiments, the XPO1 inhibitor is selected from the group consisting of the following compounds:

-continued

I-15

I-19

I-20

I-21

I-22

-continued

I-23

I-24

I-25

I-26

I-27

I-28

I-29

I-30

I-31

I-32

I-33 and pharmaceutically acceptable salts thereof.

In some embodiments, the XPO1 inhibitor is selected from the group consisting of a compound selected from the group consisting of 1-(4-methoxyphenyl)-1H-pyrrole-2,5-dione; 1-(4-bromo-2,5-difluorophenyl)-1H-pyrrole-2,5-dione; 3-methyl-1-(1-methyl-1H-pyrazol-3-yl)-1H-pyrrole-2,5-dione; 4-(2,5-dioxo-2,5-dihydro-1H-pyrrol-1-yl)-N-(5-methylisoxazol-3-yl)benzenesulfonamide; 1-(3-benzoyl-4-methylthiophen-2-yl)-1H-pyrrole-2,5-dione; 1-(4-(3-(trifluoromethyl)-1H-pyrazol-1-yl)phenyl)-1H-pyrrole-2,5-dione; 1-(4-(4-chlorophenyl)thiazol-2-yl)-3-methyl-1H-pyrrole-2,5-dione; 1-(benzo[b]thiophen-3-ylmethyl)-1H-pyrrole-2,5-dione; 1-(3,4-dimethoxyphenethyl)-1H-pyrrole-2,5-dione; 1-(naphthalen-1-yl)-1H-pyrrole-2,5-dione; 1-(4-cyclohexylphenyl)-1H-pyrrole-2,5-dione; 1-(2-benzoylphenyl)-1H-pyrrole-2,5-dione; 1-(4-morpholinophenyl)-1H-pyrrole-2,5-dione; 1-(4-chlorophenethyl)-1H-pyrrole-2,5-dione; 1-(2-(thiophen-2- yl)ethyl)-1H-pyrrole-2,5-dione; 1-([3,4] methylenedioxybenzyl)-1H-pyrrole-2,5-dione amide and pharmaceutically-acceptable salts thereof.

In some embodiments, the XPO1 inhibitor is selected from the group consisting of the following compounds:

I-3

I-4

I-5

I-6

I-7

-continued

I-8

I-9

I-10

I-11

I-12

I-13

-continued

I-14

I-15

I-16

I-17

I-18

-continued

I-19

I-20

I-21

I-22

I-23

I-24

In some embodiments, the XPO1 inhibitor is KPT-330 (Etchin J, Sanda T, Mansour M R, Kentsis A, Montero J, Le B T, Christie A L, McCauley D, Rodig S J, Kauffman M, Shacham S, Stone R, Letai A, Kung A L, Thomas Look A. KPT-330 inhibitor of CRM1 (XPO1)-mediated nuclear export has selective anti-leukaemic activity in preclinical models of T-cell acute lymphoblastic leukaemia and acute myeloid leukaemia. Br J Haematol. 2013 April; 161(1):117-27. doi: 10.1111/bjh.12231. Epub 2013 Feb. 4).

KPT-330

In some embodiments, the XPO1 inhibitor is KPT-276 (Schmidt J, Braggio E, Kortuem K M, Egan J B, Zhu Y X, Xin C S, Tiedemann R E, Palmer S E, Garbitt V M, McCauley D, Kauffman M, Shacham S, Chesi M, Bergsagel P L, Stewart A K. Genome-wide studies in multiple myeloma identify XPO1/CRM1 as a critical target validated using the selective nuclear export inhibitor KPT-276. Leukemia. 2013 Jun. 11. doi: 10.1038/leu.2013.172.).

KPT-276

An "inhibitor of expression" refers to a natural or synthetic compound that has a biological effect to inhibit the expression of a gene.

In a preferred embodiment of the invention, said inhibitor of gene expression is a siRNA, an antisense oligonucleotide or a ribozyme.

Inhibitors of gene expression for use in the present invention may be based on antisense oligonucleotide constructs. Anti-sense oligonucleotides, including anti-sense RNA molecules and anti-sense DNA molecules, would act to directly block the translation of the targeted mRNA by binding thereto and thus preventing protein translation or increasing mRNA degradation, thus decreasing the level of the targeted protein (i.e. XPO1), and thus activity, in a cell. For example, antisense oligonucleotides of at least about 15 bases and complementary to unique regions of the mRNA transcript sequence encoding the target protein can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of gene expression for use in the present invention. Gene expression can be reduced by contacting the tumor, subject or cell with a small double stranded RNA (dsRNA), or a vector or construct causing the production of a small double stranded RNA, such that gene expression is specifically inhibited (i.e. RNA interference or RNAi). Methods for selecting an appropriate dsRNA or dsRNA-encoding vector are well known in the art for genes whose sequence is known (e.g. see Tuschi, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as inhibitors of gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of the targeted mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in KRIEGLER (A Laboratory Manual," W.H. Freeman C.O., New York, 1990) and in MURRY ("Methods in Molecular Biology," vol. 7, Humana Press, Inc., Cliffton, N.J., 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hematopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g., SANBROOK et al., "Molecular Cloning: A Laboratory Manual," Second Edition, Cold Spring Harbor Laboratory Press, 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

Typically the XPO1 inhibitor is administered to the subject in a therapeutically effective amount.

By a "therapeutically effective amount" of the XPO1 inhibitor of the invention as above described is meant a sufficient amount of the compound. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidential with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The XPO1 inhibitor of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Galenic adaptations may be done for specific delivery in the small intestine or colon.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising XPO1 inhibitors of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The XPO1 inhibitor of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifusoluble agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The XPO1 inhibitor of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the XPO1 inhibitors of the invention formulated for parenteral administration, such as intravenous or intramuscular injection, other pharmaceutically acceptable forms include, e.g. tablets or other solids for oral administration; liposomal formulations; time release capsules; and any other form currently used.

A further object of the invention relates to a method for screening a drug suitable for the treatment of a myelodysplastic syndrome comprising the steps consisting of i) providing a candidate compound, ii) testing whether the candidate compound for its ability to inhibit XPO1 activity or expression and iii) selecting the candidate compound that is able to inhibit XPO1 activity or expression.

Tests and assays for determining whether a compound is a XPO1 inhibitor are well known by the skilled person in the art such as described in Etchin et al., 2013; Schmidt et al., 2013; Turner et al., 2014; Fung and Chook, 2014; Senapedis et al., 2014; Mao and Yang, 2013; Gravina et al., 2014.

The present invention also relates to a method for treating a myelodysplastic syndrome in a subject in need thereof, comprising the step of administering to said subject an XPO1 inhibitor.

The present invention also relates to a method for promoting or restoring erythrocyte maturation in a subject suffering from a myelodysplastic syndrome, comprising the step of administering to said subject an XPO1 inhibitor.

The invention will be further illustrated by the following figures and examples. However, these examples and figures should not be interpreted in any way as limiting the scope of the present invention.

EXAMPLE

Background

It has been published by our lab (Ribeil et al., Nature 2007) that Leptomycin B (LMB), a chemical inhibitor of XPO1, induces HSP70 nuclear retention in erythroid precursor cells. This observation suggests that XPO1 might be involved in the nuclear export of HSP70 protein in erythroid precursor. During erythroid precursor cell differentiation, the nuclear accumulation of HSP70 protein is essential. In fact, in the nucleus, HSP70 protects GATA1 transcription factor from Caspase 3 degradation. In case of myelodysplastic syndrome (MDS), a defect in nuclear localization of HSP70 in erythroid progenitor cells has been assessed (Frisan et al. Blood 2012, Arlet et al unpublished data). Thus, we suggest that it would be of interest to repress XPO1-induced HSP70 nuclear export to restore HSP70 protein nuclear localization in erythroid precursors cells, and therefore improve erythroid precursors differentiation. KPT-330 (Selinexor*) is the first selective inhibitor of XPO1 and producted by Karyopharm. In vitro analysis and safety studies in human patients have shown a good tolerability of the molecule. We suggest to assess the effect of KPT molecule (KPT-251 suitable for in vitro tests) in MDS erythroid precursor cells.

Material and Methods:

Material

Umbilical cord blood units from normal full-term deliveries were obtained, after informed mother's consent, from the Obstetrics Unit of Hôpital Necker-Enfants Malades. CD36+ erythroid progenitors, generated from 7 days IL-6+ IL3+SCF-cultured CD34 progenitors isolated from cord blood (Miltenyi CD34 Progenitor Cell Isolation Kit), were cultured in the presence of IL3+SCF+Epo in IMDM (Gibco cell culture) supplemented with 15% BIT 9500 (Stem Cell Technologies).

Immunoblot Analyses

Separate cytoplasmic and nuclear protein fractions were extracted from erythroid progenitors using NE-PER Nuclear and cytoplasmic extraction reagents (Thermo Scientific), following manufacturer's protocol.

40 µg of proteins of nuclear or cytoplasmic extracts were resolved on 14% acrylamide gels and analysed by immunoblotting. Antigens were visualized by chemiluminescence using SuperSignal West Dura (Thermo Scientific).

Reagents

Antibodies used are anti HDAC mouse clone 3F3 #05-814 (Millipore), anti HSP70 rabbit ADI SPA 812 (Enzo lifesciences), and anti CRM1 (XPO1) rabbit #ST1100 (Calbiochem).

Cell Permeabilisation and Labelling for Fluorescence Microscopy $5.10^4$ cells were spin on slides, acetone fixated, hydrated with cold 1×PBS 1% BSA for 30 minutes, treated with formaldehyde for 15 min (Sigma), then with methanol (Prolabo) for 10 minutes at room temperature. Cells were then permeabilized with 1×PBS 0.2% triton X100 (Sigma) for 10 min at 4° C., washed and incubated in 10% BSA for 30 minutes. They were then sequentially incubated with antibodies diluted in 1×PBS 1% BSA 0.1% tween (Sigma). Nuclei were stained with DAPI and slides were examined with a confocal laser microscope (LSM 700 Carl Zeiss).

Figure 1:
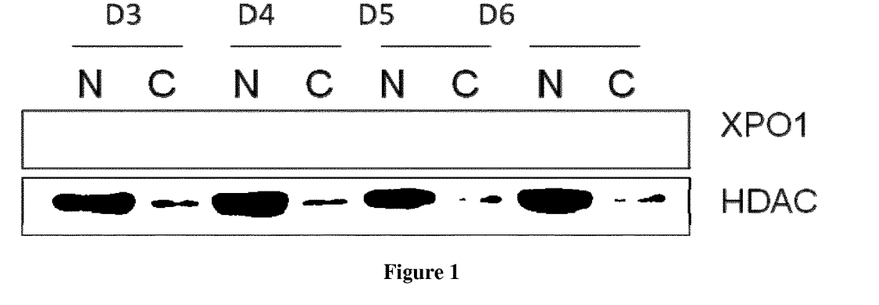
FIG. 1: Expression of XPO1 gene in CD36+ erythroid precursors (immunoblot) N=Nucleus, C=Cytoplasm. From day 3 to day 6 of CD36+ culture.
Figure 2:
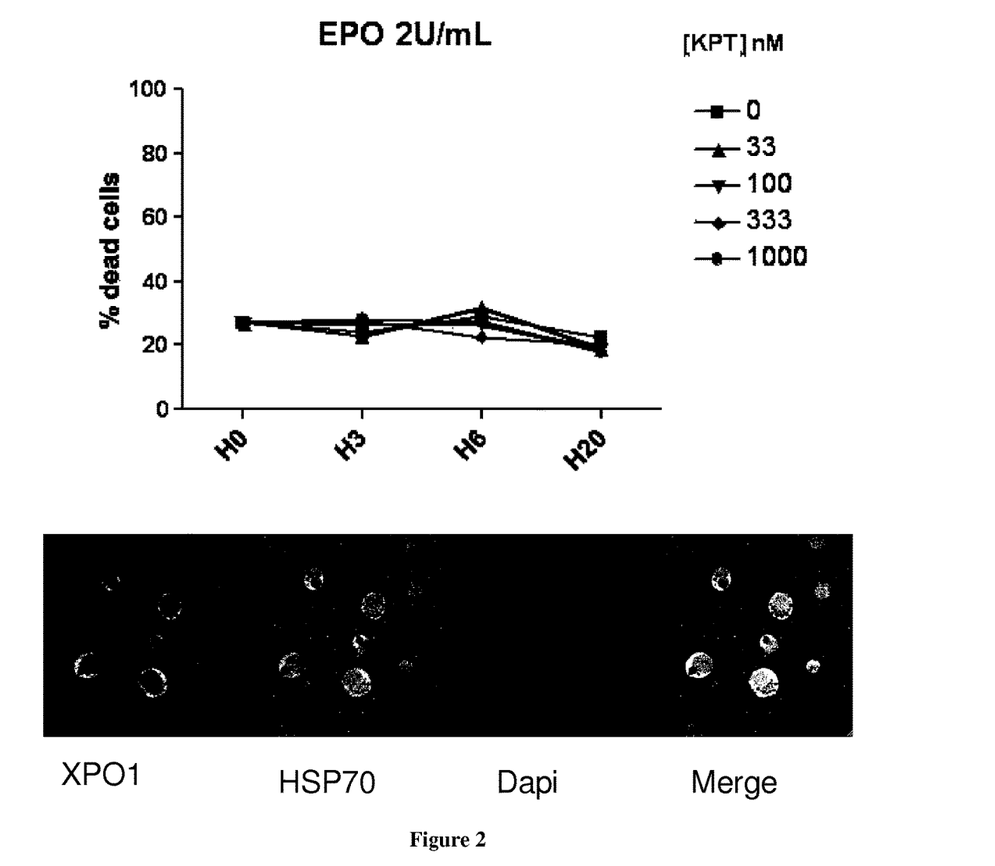
FIG. 2: Expression of XPO1 gene (and HSP70) in CD36+ erythroid precursors (fluorescence microscopy).
Figure 3A:
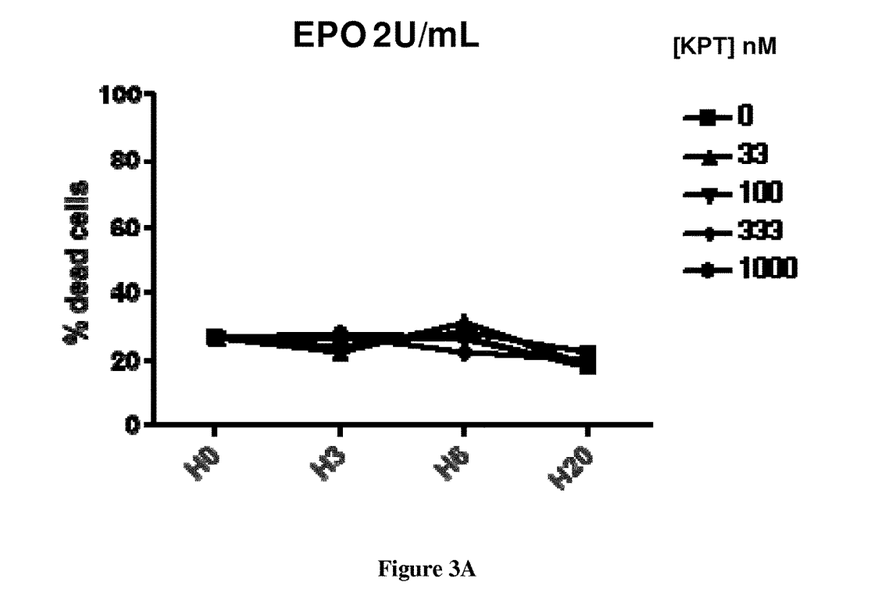
FIG. 3A. KPT is not toxic for CD36+ erythroid progenitors from cord blood at day 6 (D6) of culture, when diluted at concentrations 33 nM, 100 nM, 333 nM and 1000 nM in CD36+ culture media, with normal concentrations of erythropoietin (EPO), until 20 h of treatment.
Figure 3B:
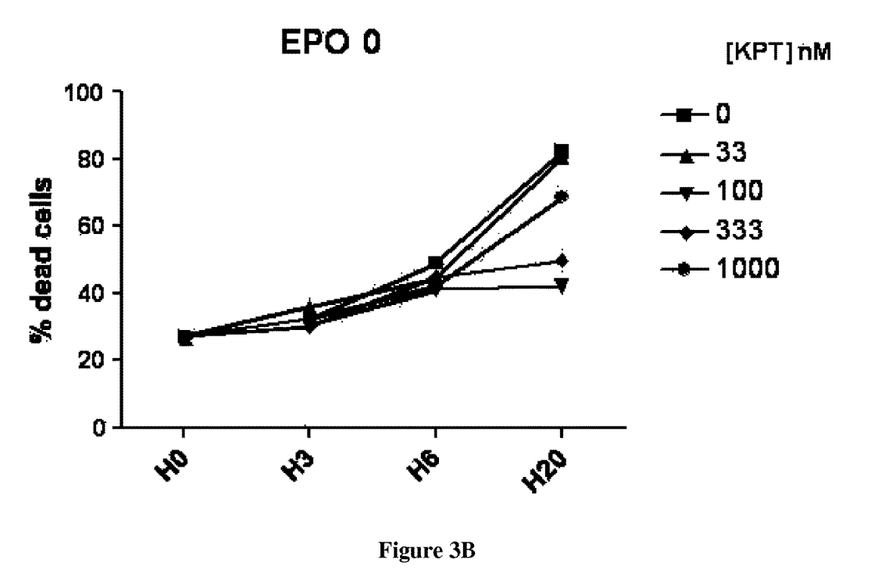
FIG. 3B. EPO starvation during 20 h results in 80% of cell death. Treatment of CD36+ D6 with KPT at 100 nM, 333 nM during EPO starvation decreases cell death, of 49% and 39% respectively, compared to the absence of KPT treatment.
Figure 4:
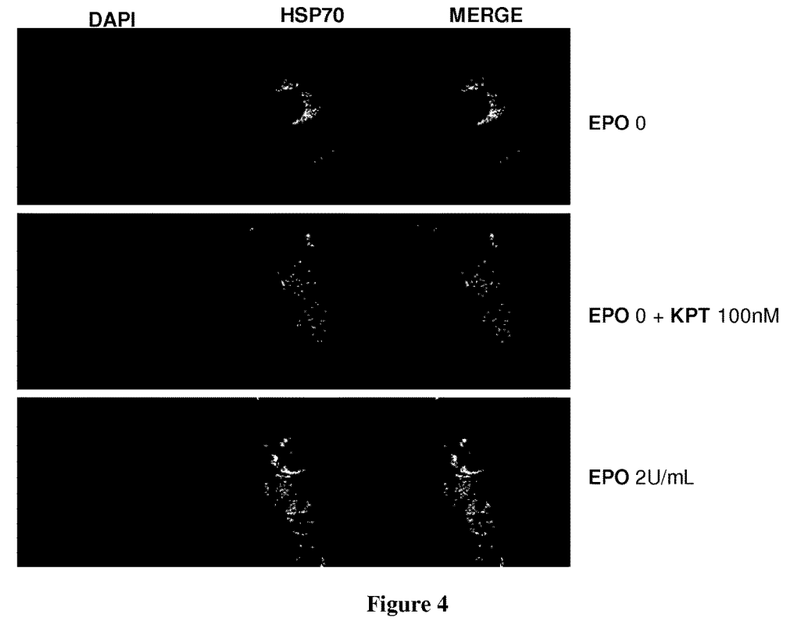
FIG. 4: KPT induces HSP70 nuclear retention in CD36+ D6 from cord blood, in conditions of EPO starvation, after 20 h of treatment.
Figure 5:
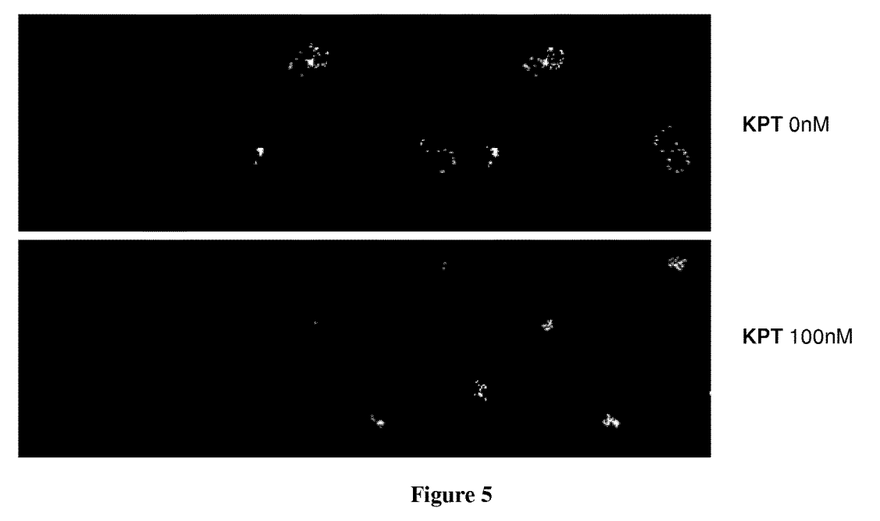
FIG. 5: In a myelodysplastic syndrome CD36+ D8 cells, KPT induces HSP70 nuclear localization after 72 h of treatment at 100 nM compared to non treated cells.
Figure 6A:
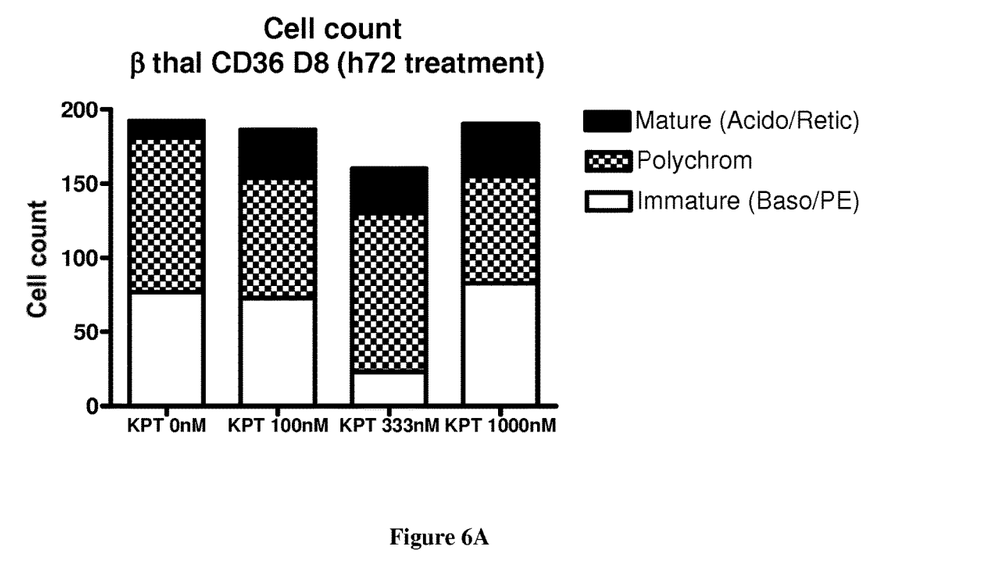
FIG. 6: In CD36+ D8 cells, KPT increases the number of mature cells (A), and the maturation index (mature*100/ polychromatic) (B), at concentrations of 100 nM, 333 nM and 1000 nM, after 72 h of treatment, compared to non treated cells (MGG observations).
Figure 6B:
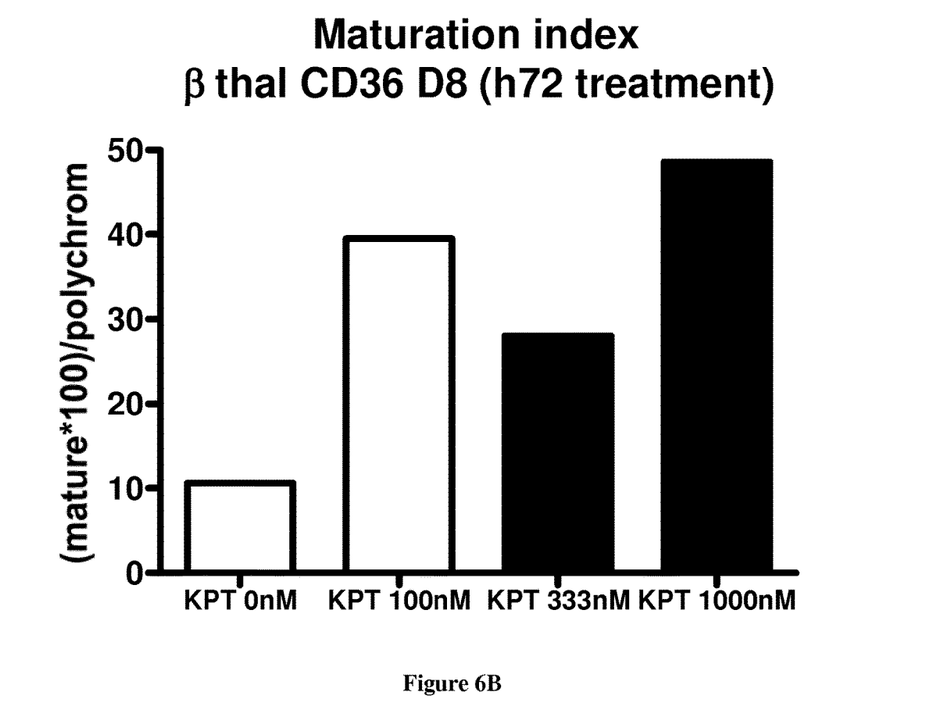

Results:

We investigated the expression of XPO1 protein in CD36+ erythroid progenitors from cord blood by immunoblot (FIG. 1) and fluorescence microscopy (FIG. 2). In FIG. 1, XPO1 protein is present majoritary in the cytoplasm (C) and to a lesser extend in the nucleus (N) compartment of CD36+ erythroid progenitors, from day 3 (D3) to day 6 (D6) of culture. In FIG. 2, the expression of XPO1 protein observed by immunoblotting is confirmed by confocal microscopy, on permeabilised CD36+ erythroid progenitors, at day 6 of culture in Epo. Here we report for the first time the expression of XPO1, a nuclear export protein of the beta importin family, in CD36+ erythroid progenitor cells.

REFERENCES

Throughout this application, various references describe the state of the art to which this invention pertains. The disclosures of these references are hereby incorporated by reference into the present disclosure.

Etchin J, Sanda T, Mansour M R, Kentsis A, Montero J, Le B T, Christie A L, McCauley D, Rodig S J, Kauffman M, Shacham S, Stone R, Letai A, Kung A L, Thomas Look A. KPT-330 inhibitor of CRM1 (XPO1)-mediated nuclear export has selective anti-leukaemic activity in preclinical models of T-cell acute lymphoblastic leukaemia and acute myeloid leukaemia. Br J Haematol. 2013 April; 161(1):117-27.

Schmidt J, Braggio E, Kortuem K M, Egan J B, Zhu Y X, Xin C S, Tiedemann R E, Palmer S E, Garbitt V M, McCauley D, Kauffman M, Shacham S, Chesi M, Bergsagel P L, Stewart A K. Genome-wide studies in multiple myeloma identify XPO1/CRM1 as a critical target validated using the selective nuclear export inhibitor KPT-276. Leukemia. 2013 Jun. 11.

Turner J G, Dawson J, Cubitt C L, Baz R, Sullivan D M. Inhibition of CRM1-dependent nuclear export sensitizes malignant cells to cytotoxic and targeted agents. Semin Cancer Biol. 2014 August; 27:62-73.

Ho Yee Joyce Fung, Yuh Min Chook. Atomic basis of CRM1-cargo recognition, release and inhibition. Seminars in Cancer Biology 27 (2014) 52-61.

William T. Senapedis, Erkan Baloglu, Yosef Landesman. Clinical translation of nuclear export inhibitors in cancer. Seminars in Cancer Biology 27 (2014) 74-86.

Lei Mao and Yongliang Yang. Targeting the Nuclear Transport Machinery by Rational Drug Design. Current Pharmaceutical Design, 2013, 19, 2318-2325.

Giovanni Luca Gravina, William Senapedis, Dilara McCauley, Erkan Baloglu, Sharon Shacham and Claudio Festuccia. Nucleo-cytoplasmic transport as a therapeutic target of cancer. Journal of Hematology & Oncology 2014, 7:85.

The invention claimed is:

1. A method for treating a myelodysplastic syndrome in a subject in need thereof, comprising the step of administering to said subject an XPO1 inhibitor.

2. A method for promoting or restoring erythrocyte maturation in a subject suffering from a myelodysplastic syndrome, comprising the step of administering to said subject an XPO1 inhibitor.

* * * * *